(12) United States Patent
MacSweeney et al.

(10) Patent No.: US 10,912,326 B2
(45) Date of Patent: Feb. 9, 2021

(54) NANOFORMULATIONS CONTAINING ENCAPSULTED OMEGA-3 FATTY ACIDS

(71) Applicants: Rachelle MacSweeney, King Township (CA); George Jackowski, King Township (CA); Paul Kerth, Pfungstadt (DE)

(72) Inventors: Rachelle MacSweeney, King Township (CA); George Jackowski, King Township (CA); Paul Kerth, Pfungstadt (DE)

(*) Notice: Subject to any disclaimer, the term of this patent is extended or adjusted under 35 U.S.C. 154(b) by 0 days.

(21) Appl. No.: 16/547,397

(22) Filed: Aug. 21, 2019

(65) Prior Publication Data

US 2020/0060321 A1  Feb. 27, 2020

Related U.S. Application Data

(60) Provisional application No. 62/721,383, filed on Aug. 22, 2018.

(51) Int. Cl.
| | |
|---|---|
| *A23L 33/115* | (2016.01) |
| *A23P 10/35* | (2016.01) |
| *B82Y 35/00* | (2011.01) |
| *B82Y 5/00* | (2011.01) |

(52) U.S. Cl.
CPC ............ *A23L 33/115* (2016.08); *A23P 10/35* (2016.08); *B82Y 5/00* (2013.01); *B82Y 35/00* (2013.01)

(58) Field of Classification Search
CPC ........ A23L 33/115; A23L 33/12; A23P 10/35; A23V 2002/00; B82Y 35/00; B82Y 45/00
See application file for complete search history.

(56) References Cited

U.S. PATENT DOCUMENTS

| | | | |
|---|---|---|---|
| 8,697,131 | B2 | 4/2014 | Tuereli et al. |
| 8,852,644 | B2 | 10/2014 | Baumstuemmler et al. |
| 9,901,893 | B2 | 2/2018 | Penth et al. |
| 2014/0004186 | A1 | 1/2014 | Hustvedt et al. |
| 2019/0030497 | A1 | 1/2019 | Baumstuemmler et al. |

FOREIGN PATENT DOCUMENTS

| | | |
|---|---|---|
| DE | 102011113413 A1 | 8/2012 |
| DE | 102013005359 A1 | 10/2014 |
| DE | 102017110292 A1 | 11/2018 |

OTHER PUBLICATIONS

Ferreira et al, Oil nanoencapsulation: development, application, and incorporation into the food market, Nanoscale Research Letters 14, Article No. 9 (2019) (Year: 2019).*
Mayo Clinic ( (Year: 2020).*

* cited by examiner

*Primary Examiner* — Carlos A Azpuru

(57) ABSTRACT

Disclosed is a method for making and using insoluble, biodegradable, nanoparticles containing the omega-3 fatty acids EPA and DHA in selected ratios. Tests show a surprising effect that the nanoformulation is twice as potent and at least five times more sustained leading to at least tenfold (2×5) higher bioavailability at equal dose (1% v/v).

8 Claims, 4 Drawing Sheets

NANOFORMULATIONS CONTAINING ENCAPSULTED OMEGA-3 FATTY ACIDS

This application claims priority to U.S. provisional application Ser. No. 62/721,383 filed on 22 Aug. 2018 the disclosure of which is hereby incorporated by reference.

FIELD OF THE INVENTION

The invention relates to methods for making stable nanoformulations containing sufficient amount of omega-3 fatty acids to elicit a biological effect when taken and the use of these nanoparticles in foods, food ingredients, beverages, supplements or drug products.

BACKGROUND OF THE INVENTION

Pharmaceutical, dietary or essential fatty acids are a family of polyunsaturated fatty acids that include the omega-3 fatty acids such as eicosapentaenoic acid (EPA) and docosahexaenoic acid (DHA), as well as omega-6 and omega-9 fatty acids. One of the primary sources for the omega-3 fatty acids is fish oil, however they can be obtained from other marine animals such squid, shrimp, krill, plants, seeds and algae.

The cardiovascular and other health benefits are now well known, in addition to their importance in nutrition. The consumption of nutritional or dietary fatty acids have been identified with many health benefits and having the potential to impact numerous diseases such as cardiovascular, neurological, immune function, and inflammation. In later life, cognitive function and brain deterioration may become a concern. Once again, maintaining high levels of EPA has been shown to lower the risk of developing and worsening cognitive decline and dementia. If someone who already has a diagnosis of dementia or Alzheimer's, their brain has already been damaged and needs structural support. At this point, DHA becomes important again and taking a high-EPA product that contains 250 mg of DHA is important to prevent further loss of brain tissue.

Omega-3 polyunsaturated fatty acids (PUFAs) containing eicosapentaenoic acid (EPA) and docosahexaenoic acid (DHA) exhibit vasoprotective effects, in part, by stimulating the endothelial formation of the potent vasoprotective factor nitric oxide (NO). A weight ratio of EPA:DHA of about 6:1 is a superior formulation.

The beneficial health effect of the omega-3 fatty acids, is especially attributed to EPA and DHA and require consumption of relatively large amounts of the omega-3 fatty acids. Depending on the purity and stability of the formulation, omega-3 fatty acid formulations often develop an unpleasant fishy aroma and taste during storage. This is attributed to the oxidation of EPA and DHA in the formulation.

Prior attempts in the food industry to add significant amounts of omega-3 fatty acids formulations directly to food products or beverages have failed unless they mask the taste or aroma with specific masking agents. Typically, this fish taste and aroma occurs either right way as the food or beverage is manufactured or within several days to weeks. It is believed that EPA and DHA are particularly unstable in the presence of water, oxygen and high heat, which are normal course components in the manufacturing of food, beverages and some pharmaceutical manufacturing processes.

It would be desirable to have a stable omega-3 fatty acid formulation containing high levels of polyunsaturated omega-3 fatty acids that are water soluble, heat and oxygen resistant and do not have fishy aroma or taste.

SUMMARY OF THE INVENTION

It is an objective of the invention to provide a consumable formulation having omega-3 fatty acids that have been encapsulated with a size within the range of about 100-2500 nm followed by a coating that enhances their stability and bioactivity.

It is a further objective of the invention to provide a method for making a highly effective, taste and odor-free formulation for omega-3 fatty acids that can be consumed directly as a nutritional supplement or blended into foods and/or drinks for enhancement of the cardiovascular value of the enhanced food or drink.

In accordance with these and other objectives that will become apparent from the description herein, a process for making encapsulated nanoformulations of omega-3 fatty acids comprises: (a) forming an emulsion comprising eicosapentaenoic acid (EPA) and docosahexaenoic acid (DHA) in a weight ratio of EPA:DHA, and (b) forming coated nanoparticles from said emulsion, wherein said nanoparticles have an average particle size within the range of 20-2500 nm.

The resulting coated nanoparticles present biologically effective EPA and DHA in a manner that is twice as potent and at least five time more sustained than control formulations. This means that the nanoformulations made by the present invention have at least a tenfold (2×5) higher bioavailability at equal dose (1% v/v), which is truly significant and unprecedented. It also means that therapeutically effective doses of one or more omega-3 fatty acid oils can be ingested with a fewer number of capsules than was possible with prior art formulations.

DETAILED DESCRIPTION

Figure 1:
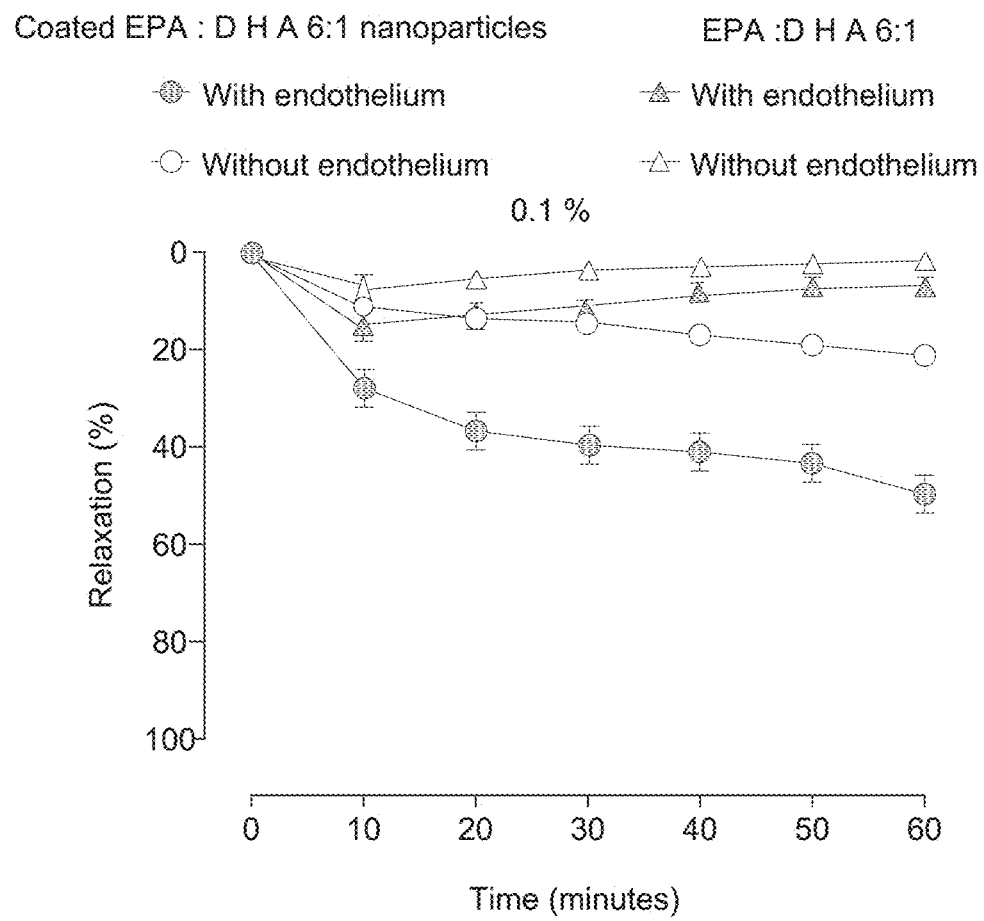
FIG. 1 is a result of tests using a concentration of 0.1%.

As used herein, the phrase "nanoformulated" is a shorthand term that refers to a material that has been reduced to an average particle size within the range of 20-2500 nm, emulsified, and then coated or encapsulated to increase stability.

It will be understood that the phrase "when taken elicits a biological effect" in the context of a consumed food refer to the serving size. If the phrase is used in the context of a beverage, it refers to the amount of nanoformulated omega-3 fatty acid per bottle or serving. If the phrase is used in the context of a drug, the phrase refers to the dose per pill or capsule.

It will be further understood in the context of the present disclosure that the phrase "Biological Effect" is measured by the Omega-3 Fatty Acid Index.

A process for making nanoformulated products according to the invention comprises: (a) forming an emulsion comprising eicosapentaenoic acid (EPA) and docosahexaenoic acid (DHA) in a weight ratio of EPA:DHA, and (b) forming coated nanoparticles from said emulsion, wherein said nanoparticles have an average particle size within the range of 20-2500 nm.

The present invention provides compositions and methods to present an odor-free, suspendable form of nanoparticles containing one or more omega-3 polyunsaturated fatty acids that can be used directly as a nutritional supplement or as an additive to a wide variety of foods, beverages, and consumed products. In particular, the invention provides a nano-encapsulated particulate comprising a core containing one or more phospholipid-stabilized EPA and DHA surrounded by a biodegradable shell wall. The manufacturing process of the invention affords the opportunity to adjust the ratios of EPA and DHA within the particulates for beneficial treatment of different disorders that can be addressed by therapeutically effective amounts of bioavailable EPA and DHA.

It has been discovered, as demonstrated in the examples, that contact of a mixture of EPA and DHA with a phospholipid dramatically reduces the perceived odor of the fatty acids while also increasing the bioavailability of the EPA and DHA. This key discovery provides a solid, soluble, nano-formulated powder that can be used to add the benefits of omega-3 fatty acids to foods.

The weight ratio of the EPA and DHA can be consumed within a wide range. For example, the nanoparticles may contain omega-3 fatty acid oils that are 100% EPA or 100% DHA based on total weight of omega-3 fatty acid oils in the nanoparticle. Alternatively, the EPA and DHA can be used as the substantially the only omega-3 fatty acid oils in the same nanoparticle having a relative weight ratio of EPA to DHA. Useful EPA:DHA ratios are within the range of 1:10 to 10:1, desirably from about 1:9 to about 9:1, more desirably from about 1:8 to about 8:1, preferably from about 1:7 to about 7:1, more preferably from about 1:6 to about 6:1, from about 1:5 to about 5:1, from about 1:4 to about 4:1, from about 1:3 to about 3:1, from about 1:2 to about 2:1, or from about 1:1 to about 2:1. A ratio of EPA:DHA of about 2:1 to 10:1, especially a ratio of about 6:1, are preferred for efficacious benefits for the consumer's cardiovascular system. An EPA:DHA ratio within the range of 1:2 to 1:1 is beneficial for infant formulations. In another embodiment, the present invention relates to nanoparticle solids comprising an encapsulated fatty acid oil mixture that comprises at least 25-100% of at least one fatty acid chosen from eicosapentaenoic acid (EPA), docosahexaenoic acid (DHA), or a combination of both, by weight of the fatty acid oil mixture, wherein the EPA and DHA are in a form chosen from ethyl ester, triglyceride and free fatty acid.

The nanoformulation of the present invention has the effect of increasing the potency of the EPA and DHA and for longer duration. Thus, the corresponding dose for the same efficacy may be roughly one-tenth (10%) of the conventional intake.

The omega-3 fatty acid oils of the present invention are stabilized with one or more phospholipids. Useful phospholipids comprise a backbone, a negatively charged phosphate group attached to an alcohol, and at least one fatty acid. Phospholipids having a glycerol backbone comprise two fatty acids and are termed glycerophospholipids. Examples of a glycerophospholipid include phosphatidylcholine, phosphatidylethanolamine, phosphatidylinositol, phosphatidylserine, and diphosphatidylglycerol (i.e., cardiolipin). Phospholipids having a sphingosine backbone are called sphingomyelins. The fatty acids attached via ester bonds to the backbone of a phospholipid tend to be 12 to 22 carbons in length, and some may be unsaturated. For example, phospholipids may contain oleic acid (18:1), linoleic acid (18:2, an omega-6), and alpha-linolenic acid (18:3, an omega-3). The two fatty acids of a phospholipid may be the same or they may be different; e.g., dipalmitoylphosphatidylcholine, 1-stearyoyl-2-myristoylphosphatidylcholine, or 1-palmitoyl-2-linoleoylethanolamine.

In one embodiment, the phospholipid may be a single purified phospholipid, such as distearoylphosphatidylcholine. In another embodiment, the phospholipid may be mixture of purified phospholipids, such as a mix of phosphatidylcholines. In still another embodiment, the phospholipid may be a mixture of different types of purified phospholipids, such as a mix of phosphatidylcholines and phosphatidylinositols or a mixture of phosphatidylcholines and phosphatidylethanolamines.

In an alternate embodiment, the phospholipid may be a complex mix of phospholipids, such as a lecithin. Lecithin is found in nearly every living organism. Commercial sources of lecithin include soybeans, rice, sunflower seeds, chicken egg yolks, milk fat, bovine brain, bovine heart, and algae. In its crude form, lecithin is a complex mixture of phospholipids, glycolipids, triglycerides, sterols and small quantities of fatty acids, carbohydrates and sphingolipids. Soy lecithin is rich in phosphatidylcholine, phosphatidylethanolamine, phosphatidylinositol, and phosphatidic acid. Lecithin may be de-oiled and treated such that it is an essentially pure mixture of phospholipids. Lecithin may be modified to make the phospholipids more water-soluble. Modifications include hydroxylation, acetylation, and enzyme treatment, in which one of the fatty acids is removed by a phospholipase enzyme and replaced with a hydroxyl group. In yet an alternate embodiment, the phospholipid may be a soy lecithin.

Preferred phospholipids for use in the present invention include phosphatidylcholine, phosphatidylethanolamine, phosphatidylinositol, and phosphatidylserine.

The amount of the phospholipid used can be within the range of 0.5-65, preferably 1-40, and most preferably 2-30 wt % of the fatty acids that are coated.

The EPA and/or DHA particulates are formed by contact with one or more suitable surfactants and gums under turbulent mixing conditions to form the insoluble, biodegradable nanoparticles of the present invention. A particularly successful method for encapsulating the EPA and DHA is by forming micelles in a water-in-oil emulsion, using a polymerizable surfactant such as acrylamide. The surfactant is polymerized in various ways, as by x-ray or gamma radiation. Suitable gums include gum arabic and other gums that are generally regarded as safe by the US Food and Drug Administration.

A preferred method for making the coated nanoparticles of the present invention is found in U.S. Pat. No. 8,852,644, the disclosure of which is hereby incorporated by reference. Briefly summarized, that process produces nanoparticles of water-soluble and water-insoluble substances by controlled precipitation, co-precipitation and self-organization processes in a microjet reactor of colliding jet streams of agents. In a first jet stream, a solvent containing at least one target molecule collides with a second jet stream of a nonsolvent. As the jets collide with each other in the microjet reactor at pressures and flow rates that form turbulent mixing conditions, the target molecule becomes enveloped in the coating material and rapidly precipitates, co-precipitates or a chemical reacts thereby forming microparticles or nanoparticles.

The particle size be controlled by the temperature at which the solvent and nonsolvent collide, the flow rates of the solvent and the nonsolvent, and/or the amount of gas in the microreactor. Smaller particle sizes are generally obtained at lower temperatures, high solvent and nonsolvent flow rates, and/or in the complete absence of gas.

The method of the present invention produces nanoparticles of water-soluble and water-insoluble substances by controlled precipitation, co-precipitation and self-organization processes in microjet reactors in which a first microjet of solvent containing at least one target molecule collides with a second microjet of a nonsolvent in a microjet reactor volume at a defined pressure and flow rate. The colliding jets effect very rapid precipitation, co-precipitation, or a chemical reaction during which the desired microparticles or nanoparticles are formed in a suspension of the particulate product in a mix of solvent and nonsolvent. The solvent and nonsolvent are removed by evaporation thereby leaving the desired particulate product.

The desired particle size range of the particulate product from the present process is small with a narrow distribution. The size and distribution are controlled by the temperature at which the solvent and nonsolvent collide, the flow rates of the solvent and the nonsolvent, and/or the amount of gas.

The first microjet contains a solvent for the target molecule of interest and any additional components or auxiliary components that should be found in the nanoparticle product. In the present case, that target molecule includes the omega-3 fatty acids as only EPA, only DHA, or a mixture in the desired ratio of EPA:DHA. In one embodiment, the first microjet stream contains only the omega-3 fatty acids and a solvent with no other additives or ingredients. In another embodiment, the first microjet stream contains one or more ingredients used to form the coating that encapsulates the omega-3 oils and any stabilizing agents or surfactants. In a further embodiment, the first microjet contains all of the ingredients in solution that will spontaneously form the desired nanoparticles upon contact with the nonsolvent in the second microjet stream.

Suitable solvents for the omega-3 fatty acid of the invention are organic, e.g., tetrahydrofuran (THF), ethanol, acetone or a mixture of acetone:ethanol 50/50 (v/v). A preferred solvent formulation contains a mixture of ethanol, polysorbate, polyoxyethylene sorbitan monopalmitate (Tween 20), and polycaprolactone.

The second microjet contains a nonsolvent, optionally containing one or more auxiliary agents. Suitable nonsolvents include water, polysorbents and stabilizing agents such as poloxamers 127, 182, 184, 188, 338, 401, 402 or 407 or poloxamines 904, 908, 1107 or 1307 the concentrations of which depend on the dissolution characteristics and the partition coefficient (log P) between the aqueous and lipid phase of the active pharmaceutical ingredient developed in a nanoparticle dosage format.

Poloxamers are nonionic triblock copolymers composed of a central hydrophobic chain of polyoxypropylene (poly(propylene oxide)) flanked by two hydrophilic chains of polyoxyethylene (poly(ethylene oxide)). For the generic term poloxamer, these copolymers are commonly named with the letter P (for poloxamer) followed by three digits: the first two digits multiplied by 100 give the approximate molecular mass of the polyoxypropylene core, and the last digit multiplied by 10 gives the percentage polyoxyethylene content (e.g. P407=poloxamer with a polyoxypropylene molecular mass of 4000 g/mol and a 70% polyoxyethylene content). The preferred second microjet contains primarily water.

The weight ratio of target molecule in the first microjet stream to any auxiliary agent in the second microjet stream is preferably at least 1:100, more preferably within the range of 1:100-1:100,000, and even more preferably within the range of 1:200-1:75,000.

The microjet reactor used in the present process has at least two nozzles oriented to impinge their respective flow streams at an angle within the range of 90° to 180° relative to the other. Each nozzle has its own pump and feed line for injecting one liquid medium into a central reactor chamber within a reactor housing to a shared collision point. The reactor housing can be provided with a first opening through which a gas can be introduced so as to maintain the gaseous atmosphere within the reactor chamber at the collision point of the liquid jets. The gas line can also help to cool the resulting products. An exhaust opening is also provided that provides an exit for the resulting products and any excess gas. The reactor housing is preferably submerged and substantially completely surrounded by a water bath that can help to control the temperature within the reactor.

It is possible to use two microjet reactors in series to provide the nanoparticles produced in the first reactor with an external coating in the second reactor, such as those resistant to gastric acids. The resulting coated nanoparticle may then be adjusted for the desired release timing after ingestion.

The temperature at which the liquids collide is one mechanism for control of the resulting particle size. Lower temperatures lead to decreasing particle sizes. In general, a desirable temperature is within the range of 25°–95° C., preferably within the range of 40°-80° C., and even more preferably within the range of 50-75° C.

Smaller particle sizes are also obtained by reducing the amount of gas, right through to a complete absence thereof, in the reactor chamber.

Preferably, there is little air or inert gas in the collision chamber. Increasing amounts of air can influence interactions between the developing diffusion layers such that, in many applications, relatively large nanoparticles are ultimately formed and can lead to undesired crystal growth. Conversely, it was surprisingly found that a complete absence of air or inert gas led to the formation of smaller particles of a narrower size distribution. If no added stream of gas is used, the rapid precipitation of particles ends as soon as the liquid jets reach the outer periphery of the liquid disc formed when they collide as impinging jets. This presumably results in early termination of particle growth and in smaller particles showing homogeneous particle distribution.

Particle size may also be controlled via solvent and nonsolvent flow rates. Namely, smaller particles are obtained by selecting a high flow rate while larger particles result when selecting a low flow rate.

The solvent and non-solvent streams preferably each independently have a flow rate of greater than 0.1 ml/min and produce impinging jets that collide at a relative speed of greater than 25 m/s, more preferably within the range of 50-350 m/s with a Reynolds number at collision of more than 100, preferably more than 500, to obtain turbulent, rapid mixing at the collision point. A useful molar range of omega-3 fatty acid solvent to nonsolvent is within the range of 0.1-100.

The solvent and nonsolvent nozzles are preferably smaller than 1,000 µm, more preferably smaller than 500 µm, and highly preferred to have an opening of smaller than 300 µm and have a driving pressure of at least 0.2 bar, preferably within the range of 0.5-100 bar and even more preferably within the range of 0.75-25 bar, the pressure being controlled by a pressure regulator associated with the feed stream to each of the first and second microjet nozzles.

The resulting coating is both insoluble in water and biodegradable in the human gut after consumption. Insolubility in water allows the coated nanoparticles to be added to foods and liquids without storage degradation or release of odors. The coating is biodegradable so that the nanoparticles to break down in a controlled manner after consumption so that the EPA and DHA are released following consumption for assimilation by the body. Preferably, the molar ratio of polymeric coating to the sum of all encapsulated omega-3 fatty acids is within the range of 0.5 to 5000.

In the event that two polymers (e.g., Polymer A and Polymer B) are used to form the encapsulation coating, the molar ratio of Polymer A to Polymer B is preferably within the range of 1:200 to 200:1 with each polymer solution exhibiting a concentration within the range of 0.01 mg/mL to 10 mg/mL.

While not wishing to be bound by theory, the enhanced potency and duration exhibited by the present invention may be the result of protection of the EPA and DHA in the core through the acidic conditions of the human stomach for release at a more optimal time in the intestinal tract.

The resulting coated nanoparticles of the present process exhibit an average particle size within the range of 20-2500 nm. Preferably, the coated nanoparticles have an average size within the range of 25-1000 nm, and especially an average size within the range of 100-500 nm, and are sufficiently small to be suspended in beverages without discernible notice or detection by the consumer.

The particle size distribution of coated omega-3 acids made according to the invention have a narrow particle size distribution that is believed to enhance the bioavailability of the omega-3 fatty acids. A suitable average particle size for the encapsulated omega-3 fatty acids of the inventions is within the range from about 25-2500 nm, preferably an average particle size within the range of 25-1000 nm, and an especially preferred particle size distribution is an average particle size within the range of 100-500 nm. The polydispersity index (PDI) of the generated particles is generally below 2.0, preferably below 1.0, more preferably below 0.5, and most preferably below 0.4. This makes for an optimal size for bioavailability and treatment according to the invention.

It will be understood that the recitation of a numerical range in this application is also implicitly intended to disclose and support the recitation of each individual number within the specified range at the degree of precision expressed by the number of significant digits used to identify the range less any trailing zeroes, e.g., disclosing the range of 0.09-0.15 is intended to disclose the individual numbers 0.09, 0.10, 0.11, 0.12, 0.14, and 0.15 while a range of 0.1-100 is intended to disclose 0.1, 0.2, 0.3, . . . 99.8, 99.9, and 100.

In physical and organic chemistry, the dispersity is a measure of the heterogeneity of sizes of molecules or particles in a mixture. A collection of objects is called uniform if the objects have the same size, shape, or mass. A sample of objects that have an inconsistent size, shape and mass distribution is called non-uniform.

The polydispersity index uses dynamic light scattering under the cumulant method to measure the size distribution variance profile of small particles (<250 nm) in suspension. With the dynamic light scattering measurement technique, the dispersity values of small particles in suspension are generally in the range from 0 (uniform size) to 1 (non-uniform size).

Preferably, the nanoparticles of omega-3 fatty acids according to the invention are coated with one or more polymers that stabilize the particle against premature degradation. The process of coating of the formed omega-3 nanoparticles is made during a one-step formation process in which the omega-3 fatty acids in a liquid form at the appropriate rate are dissolved in one or more organic solvents to which are added coating agents, such as plant or animal-based gelatin, synthetic or natural gum derivatives, e.g. arabic gum or pectin.

Suitable polymers that can be used as such coatings, their respective concentrations as introduced into the microjet chamber and impacted as directed by the present specification. The result is a suspension of coated or encapsulated particulates containing EPA and DHA at the ratio of the incoming stream with a small size (e.g., 100-500 nm) and very narrow particle size distribution, e.g., a PDI or less than about 1, desirably less than about 0.75, more desirably within the range of with polydispersity index within the range of 0.001 to less than 0.25, preferably within the range of 0.005-0.20, and especially preferred of a PDI within the range of 0.005-0.15 at a 95% confidence interval. Such a narrow particle size distribution of nanoparticles provides an excellent source of bioavailable omega-3 fatty acids at a high potency.

Examples of produced nanoparticles according to the invention with their size range at 95% confidence, average PDI, and PDI standard deviation are listed in Table 1.

TABLE 1

| Polymer | Concentration (mg/ml) | Nanoparticle Size Range (95% CI) | Average Polydispersity Index (PDI) | PDI Standard Deviation |
| --- | --- | --- | --- | --- |
| Polypropylcyanoacrylate | 0.05-5.0 | 100-480 nm | 0.15 | 0.011 |
| Polylactic co-glyconic acid (PLGA) | 0.05-5.0 | 100-450 nm | 0.19 | 0.015 |
| Sulfobutylated polyvinylalcohol-PLGA | 0.025-5.0 | 120-480 nm | 0.12 | 0.01 |
| Lectin-PLGA | 0.025-5.0 | 125-475 nm | 0.20 | 0.016 |
| Gliadin | 0.025-5.0 | 100-430 nm | 0.17 | 0.015 |
| Lectin-Gliadin | 0.025-5.0 | 120-485 nm | 0.19 | 0.017 |
| Chitosan | 0.01-4.0 | 100-475 nm | 0.21 | 0.017 |
| Polyethyleneglycolpolylactic acid | 0.05-5.0 | 130-490 nm | 0.18 | 0.014 |
| Polyethylenemethacrylate (PMMA) | 0.05-5.0 | 100-445 nm | 0.16 | 0.013 |
| Polymethylvinylether-co-maleic anhydride | 0.01-5.0 | 140-490 nm | 0.22 | 0.018 |
| Polyethylene oxide - polyoxypropylene (PEO-POP) | 0.01-5.0 | 110-460 nm | 0.15 | 0.011 |

TABLE 1-continued

| Polymer | Concentration (mg/ml) | Nanoparticle Size Range (95% CI) | Average Polydispersity Index (PDI) | PDI Standard Deviation |
|---|---|---|---|---|
| Poly N-isopropylacrylamide | 0.05-5.0 | 135-485 nm | 0.20 | 0.017 |
| Poly N-vinylacetamide | 0.05-5.0 | 120-475 nm | 0.15 | 0.010 |
| Poly t-butylmethacrylate | 0.05-5.0 | 100-475 nm | 0.23 | 0.018 |
| Polycaprolactone (PCL) | 0.05-5.0 | 115-470 nm | 0.22 | 0.017 |
| Gelatin (plant or animal based) | 0.01-5.0 | 100-490 nm | 0.19 | 0.014 |
| Polystyren | 0.05-5.0 | 100-475 nm | 0.21 | 0.017 |
| Hydroxypropylmethylcellulose phthalate (HPMCP 50) | 0.5-15.0 | 100-475 nm | 0.20 | 0.013 |
| Hydroxypropylmethylcellulose phthalate (HPMCP 55) | 0.25-15.0 | 100-475 nm | 0.21 | 0.016 |
| Methacrylic acid/Ethylacrylate co-polymers: | | | | |
| Eudragit S 100* (anionic polymer, increasing bioavailability) | 0.25-10.0 | 100-495 nm | 0.24 | 0.019 |
| Eudragit E 100** (cationic polymer, decreasing bioavailability) | 0.25-10.0 | 100-475 nm | 0.23 | 0.017 |

*EUDRAGIT S 100 is an anionic copolymer based on methacrylic acid and methyl methacrylate having the chemical name Poly(methacylic acid-co-methyl methacrylate) 1:2. It is available from Evonik Corporation in Parsippany, NJ.
**EUDRAGIT E100 is a cationic copolymer based on dimethylaminoethyl methacrylate, butyl methacrylate, and methyl methacrylate with the chemical name of Poly(butyl methacrylate-co-(2-demethylaminoethyl) methacrylate-co-methyl methacrylate) 1:2:1. It is available from Evonik Corporation in Parsippany, NJ.

Preferably, the molar ratio of polymeric coating to contained omega-3 fatty acid is within the range of 0.5-5000. In the event that two polymers are used to coating the core omega-3 fatty acid, the molar ratio of the first polymer to the second polymer is preferably within the range of 1:200 to 200:1 with the first and second polymers each independently having a concentration within the range of 0.01 mg/ml to 10 mg/ml.

If desired, the coated nanoparticles of the present invention can include a pH buffer such as trisodiumphosphate at a concentration of 0.05-0.5 M to buffer the composition at a pH within the range of 6.7-7.1.

The coated nanoparticles of omega-3 fatty acids according to the invention may also contain one or more stabilizing agents or surfactants. A suitable list of such ingredients and their useful concentration ranges are found in Table 2.

TABLE 2

| Agent | Concentration |
|---|---|
| Poloxamer 182 | 0.5-10.0 mg/mL |
| Poloxamer 184 | 0.5-10.0 mg/mL |
| Poloxamer 188 | 0.5-10.0 mg/mL |
| Poloxamer 338 | 0.5-10.0 mg/mL |
| Poloxamer 401 | 0.5-10.0 mg/mL |
| Poloxamer 402 | 0.5-10.0 mg/mL |
| Poloxamer 407 (Pluronic ® F127) | 0.5-10.0 mg/mL |
| Poloxamine 904 | 0.5-10.0 mg/mL |
| Poloxamine 908 | 0.5-10.0 mg/mL |
| Poloxamine 1107 | 0.5-10.0 mg/mL |
| Poloxamine 1307 | 0.5-10.0 mg/mL |
| Polyvinylalcohol (PVA) | 0.05-2.0 vol % |
| Polyvinylpyrrolidone (PVP) | 0.05-2.0 vol % |
| Hydroxypropylcellulose (HPC) | 0.05-0.75 vol % |
| Hydroxypropylmethylcellulose (HPMC) | 0.05-2.0 vol % |
| Polysorbate 20 (Tween ® 20, polyoxyethylene sorbitan monopalmitate) | 0.01-0.75 vol % |
| Polysorbate 40 | 0.01-0.75 vol % |
| Polysorbate 60 | 0.01-0.75 vol % |
| Polysorbate 65 | 0.01-0.75 vol % |
| Polysorbate 80 | 0.01-0.75 vol % |
| Polysorbate 85 | 0.01-0.75 vol % |

The coated nanoparticles of the present invention can be added to a wide variety of foods and beverages to provide the benefits of EPA and DHA without having to consume a pill or capsule. Exemplary foods and liquids that can be enhanced by addition of the nanoparticles of the present invention include food is in the form of (a) meat products, such as sausages, cooked ham, cooked turkey, cured sausages, pork loin, and cured ham, (b) baked goods such as breads, bread crumbs, cookies, and crackers, (c) snack foods such as salty snacks, specialty snacks, confectionary snacks, soft candies, chocolates, gummy candy, marshmallows, natural occurring snack foods, ready to eat cereals, trail mixtures, chips, granola bars, and toaster pastries, (d) emulsions and suspensions such as condiments, ketchup or mustard, salad dressing, mayonnaise, soups, fruit preservatives, jams, puddings (e) baking ingredients such as corn flour, wheat flour, rice flour, potato flour, (f) pasta, (g) spreads such as butters, margarine, peanut butters, (h) canned meats with or without sauces such as pet foods, (i) beverages such as liquid milk beverages, *lactobacillus* beverages, carbonated beverages, fruit-containing beverages, fruit juices, soft drinks, energy drinks, sport drinks, vitality drinks, nutritional supplement drinks, vegetable-containing drinks, alcohol-containing mixed drinks, beers, wine, liqueurs, coffees, coffee drinks, or teas, (j) seasoning and flavor agents, spices, and (k) ingredients used to make these foods.

The coated nanoparticles of the present invention can also be presented in the form of nutritional supplement or drug pills or capsules having a daily dosage within the range of 10 μg-1000 mg. In such an embodiment, the suspension of formed nanoparticles from the microreactor is concentrated and/or dried to a form that is suitable for loading into a capsule or formulation into an ingestible pill.

EXAMPLES

Example 1—Preparation

In the present invention nanoparticles were prepared according to an optimized nanoprecipation method described in U.S. Pat. No. 8,852,644, Oct. 7, 2014—Method and Device for Producing Microparticles or Nanoparticles, Baumstuemmler et al. (the disclosure of which is hereby incorporated by reference by utilizing the microjet reactor (MJR) developed by Instillo GMBH, Saarlouis (DE) with solvents optimized for omega-3 fatty acids. The omega-3 fatty acid used in this example was a high purity greater than 90% EPA:DHA 6:1 omega-3 ethyl esters formulation.

The EPA:DHA in a weight ratio of about 6:1 was emulsified in water phase using phosphatidylcholine and other surfactants. Proteins and gum derivatives were then added to the emulsion form the coating on the omega-3 nanoparticles when the break from the emulsion.

Example 2—Characterization

The emulsification and coating protocols resulted in stable, encapsulated, EPA:DHA 6:1, nanoparticles with a particle size of 287.8 nm and a particle distribution size (PDI) of 0.107, which were similar after storage for 7 days at room temperature (particle size of 293.4 nm with a PDI value of 0.215) demonstrating the absence of leakage from particles.

The resulting nanoparticles are water soluble. When added to water or beer, the beverages had no fishy taste or aroma and the nanoparticles are heat resistant.

Example 3—Efficacy

And amount of omega-3 fatty acids in a weight ratio of EPA:DHA of 6:1 was emulsified in water phase using phosphatidylcholine and other surfactants, and then coated with proteins and gum derivatives to increase the stability and dispersibility of the coated omega-3 nanoparticles emulsion as in Example 1. The nanoformulation was then tested for its effects on nitric acid in porcine coronary artery rings.

Porcine coronary artery rings with and without endothelium were contracted with thromboxane $A_2$ analogue U46619 to about 70% of the maximal contraction induced by high potassium solution before the addition of a single concentration of an omega-3 preparation containing coated and uncoated particles containing EPA and DHA in a weight of 6:1 according to the invention. Thereafter, changes in vascular tone were assessed over a 60 minute period. The results were expressed as a percentage of relaxation and reported as means±SEM (n=5 each group).

Figure 2:
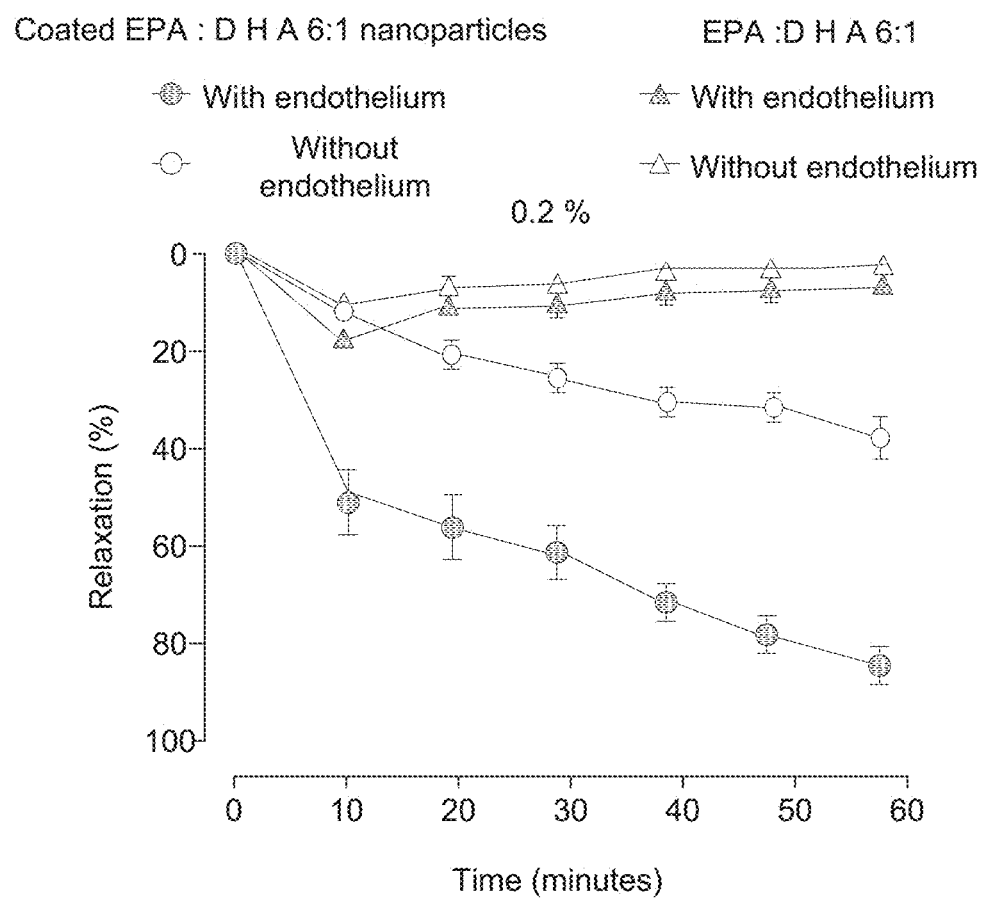
FIG. 2 is a result of tests using a concentration of 0.2%.
Figure 3:
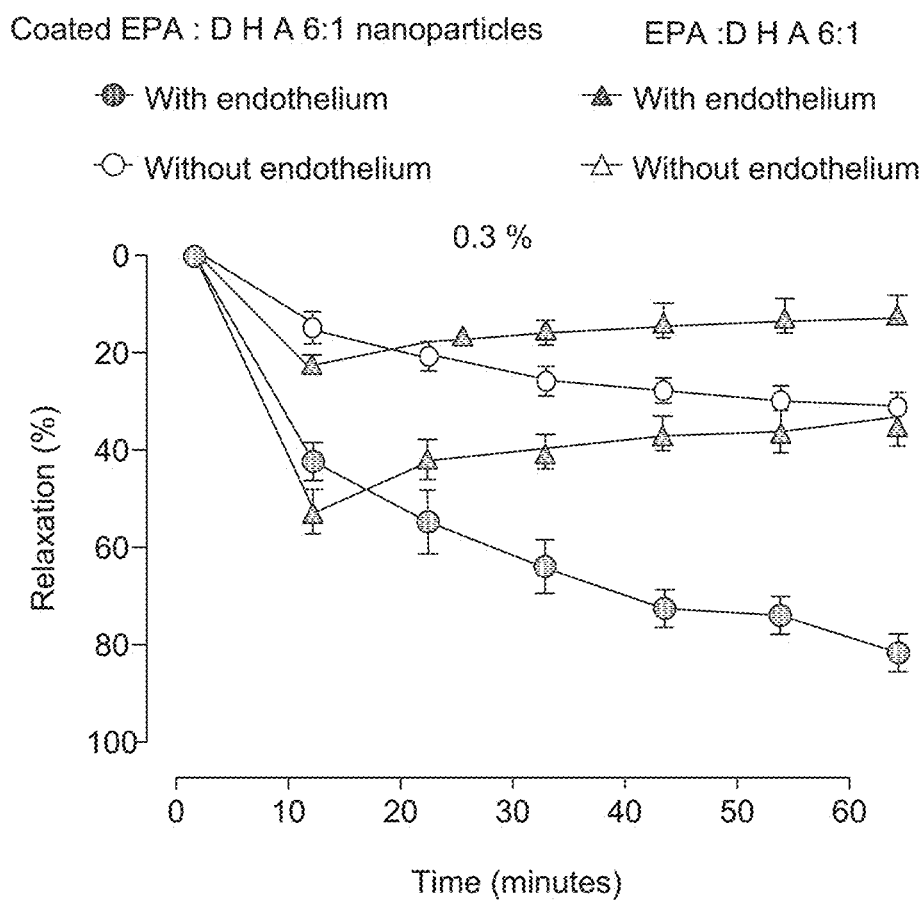
FIG. 3 is a result of tests using a concentration of 0.3%.
Figure 4:
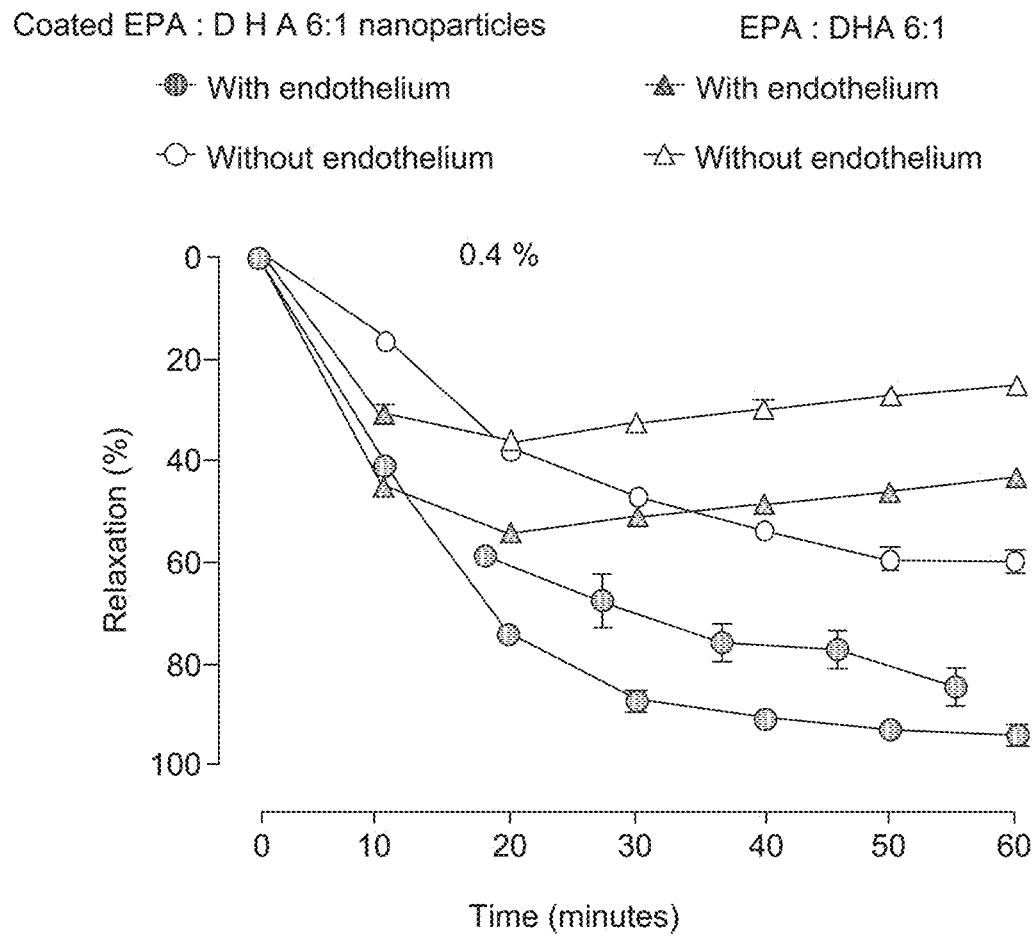
FIG. 4 is a result of tests using a concentration of 0.4%.

Any changes in the isometric tension of porcine coronary artery rings were determined using organ chambers. The role of nitric oxide was assessed using NG-nitro L-arginine (L-NA, NO synthase inhibitor), prostanoids using indomethacin (Indo, cyclooxygenases inhibitor), and endothelium-derived hyperpolarization (EDH) using TRAM-34 and UCL-1684 (calcium-dependent potassium channel inhibitors). The results measured in terms of relaxation % v. time (minutes) at 20 and 60 minutes for each of the concentrations are shown in Table 3. Full results are illustrated in FIGS. 1-4.

TABLE 3

| | 0.1% | | 0.2% | | 0.3% | | 0.4% | |
|---|---|---|---|---|---|---|---|---|
| | 20 m | 60 m | 20 m | 60 m | 20 m | 60 m | 20 m | 60 m |
| Coated with endothelium | 27 | 49 | 50 | 86 | 45 | 84 | 41 | 95 |

TABLE 3-continued

| | 0.1% | | 0.2% | | 0.3% | | 0.4% | |
|---|---|---|---|---|---|---|---|---|
| | 20 m | 60 m | 20 m | 60 m | 20 m | 60 m | 20 m | 60 m |
| Coated without endothelium | 10 | 20 | 12 | 40 | 12 | 31 | 16 | 60 |
| Uncoated with endothelium | 15 | 6 | 19 | 5 | 55 | 36 | 45 | 43 |
| Uncoated without endothelium | 6 | 2 | 11 | 2.5 | 23 | 11 | 31 | 25 |

Results:

The coated EPA:DHA 6:1 nanoparticles caused greater sustained endothelium-dependent relaxations than the non-formulated EPA:DHA 6:1 whereas at higher concentrations both preparations caused endothelium-independent relaxations.

The endothelium-dependent relaxation to the coated EPA:DHA 6:1 nanoparticles was markedly inhibited by L-NA, partially by TRAM-34 and UCL-1684 and not affected by indomethacin. In contrast, the endothelium-dependent relaxation to the non-formulated EPA:DHA 6:1 was inhibited by L-NA, TRAM-34 and UCL-1684, and also by indomethacin.

When the nanoformulated, coated EPA:DHA 6:1 was compared to nanoformulated, uncoated EPA:DHA 6:1 for their biological activity on isolated coronary arteries, the coated formulation induced twice as high vasodilation and increased the time of sustained vasodilation five times. The surprising effect is that the present nanoformulation is twice as strong and at least five times more sustained leading to at least tenfold (2×5) higher bioavailability at equal dose (1% v/v), which is truly significant and unprecedented.

The invention claimed is:

1. A composition comprising an aqueous suspension of a nanoparticles that comprise at least one omega-3 fatty acid oil that is encapsulated by a coating agent, wherein said at least one fatty acid oil comprises eicosapentaenoic acid (EPA) and/or docosahexaenoic acid (DHA) wherein the EPA and/or DHA are in a form chosen from ethyl ester, triglyceride and free fatty acid;
   wherein the suspension of nanoparticles is made by a process that comprises impacting at least (a) a first fluid stream comprising a mixture of EPA and DHA with a solvent for omega-fatty acid oils against (b) a second fluid stream comprising water in a microreactor at a temperature and flow rate of each stream sufficient to produce said suspension of encapsulated EPA and DHA at an average particle size;
   wherein the fatty acid nanoparticles in the suspension have an average particle size within the range of 25-500 nm and that exhibits a polydispersity index (PDI) within the range of less than 0.40.

2. A composition according to claim 1 wherein the fatty acid oil is a mixture of EPA and DHA having a higher concentration by weight of EPA than DHA; the coating agent comprises a gelatin, a gum derivative or a polymer; and the particulates further comprise one or more stabilizing agents or surfactants.

3. A composition according to claim 2, wherein the coating agent comprises a chitosan, gelatin, gliadin, lectin-gliadin, methacrylic acid/ethylacrylate co-polymer, polypropylcyanoacrylate, polylactic co-glyconic acid (PLGA), sulfobutylated polyvinylalcohol-PLGA, lectin-PLGA, polyethyleneglycolpolylactic acid, polyethylenemethacrylate (PMMA), polymethylvinylether-co-maleic anhydride, polyethylene oxide-polyoxypropylene (PEO-POP), poly(N-isopropylacrylamide), poly(N-vinylacetamide), poly(t-butylmethacrylate), polycaprolactone (PCL), polystyrene, or hydroxypropylmethylcellulose phthalate.

4. A composition according to claim 1 wherein the at least one omega-3 fatty acid oil comprises a mixture of EPA and DHA at a weight ratio of EPA:DHA within the range of about 1:2 to about 10:1.

5. A composition according to claim 1 wherein the nanoparticle solids in suspension comprise an encapsulated fatty acid oil mixture that comprises 25-100% of at least one fatty acid chosen from eicosapentaenoic acid (EPA) and docosahexaenoic acid (DHA).

6. A composition according to claim 1 wherein the composition is in the form of an encapsulated nanoparticle having a size within the range of 100-500 nm, and the coating agent comprises a gelatin, a gum derivative or a polymer.

7. A composition according to claim 1 wherein the fatty acid oil nanoparticles comprise a mixture of EPA and DHA, and further comprises at least one other fatty acid other than EPA and DHA in a form chosen from ethyl ester, triglyceride and free fatty acid.

8. A composition according to claim 1 further comprising a food, beverage, or consumable capsule having said suspension incorporated therein.

* * * * *